United States Patent
Tobinick

(10) Patent No.: US 6,423,321 B2
(45) Date of Patent: *Jul. 23, 2002

(54) CYTOKINE ANTAGONISTS FOR THE TREATMENT OF SENSORINEURAL HEARING LOSS

(76) Inventor: Edward L. Tobinick, 100 UCLA Medical Plz., Suite 205, Los Angeles, CA (US) 90024-6903

( * ) Notice: Subject to any disclaimer, the term of this patent is extended or adjusted under 35 U.S.C. 154(b) by 0 days.

This patent is subject to a terminal disclaimer.

(21) Appl. No.: 09/749,189

(22) Filed: Dec. 27, 2000

Related U.S. Application Data

(63) Continuation-in-part of application No. 09/654,996, filed on Sep. 5, 2000, which is a continuation-in-part of application No. 09/563,651, filed on May 2, 2000, which is a continuation-in-part of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.[7] ................................................. A61K 9/00
(52) U.S. Cl. ....................... 424/400; 424/422; 424/434; 424/427; 424/134.1; 514/898; 514/885; 514/913; 514/914
(58) Field of Search ............................. 424/422, 134.1, 424/400, 427, 434; 514/362, 363, 364, 898, 885, 913, 914

(56) References Cited

U.S. PATENT DOCUMENTS

| | | | |
|---|---|---|---|
| 5,075,222 A | 12/1991 | Hannum et al. | 435/69.1 |
| 5,385,901 A | 1/1995 | Gilla et al. | 514/231.5 |
| 5,434,170 A | 7/1995 | Andrulis | 514/323 |
| 5,525,621 A * | 6/1996 | Burt et al. | 514/393 |
| 5,559,114 A | 9/1996 | Exley | 514/261 |
| 5,605,690 A | 2/1997 | Jacobs et al | 424/134.1 |
| 5,656,272 A | 8/1997 | Le et al. | 424/133.1 |
| 5,837,681 A | 11/1998 | Magal | 514/12 |
| 5,863,769 A | 1/1999 | Young | 435/69.52 |
| 6,043,221 A | 3/2000 | Magal et al. | 514/12 |
| 6,124,322 A | 9/2000 | Bjoerkman | 514/323 |
| 6,180,355 B1 * | 1/2001 | Alexander et al. | 435/7.1 |

* cited by examiner

Primary Examiner—Thurman K. Page
Assistant Examiner—Lakshmi Channavajjala
(74) Attorney, Agent, or Firm—Ezra Sutton

(57) ABSTRACT

Specific Cytokine Antagonists, including TNF antagonists and/or Interleukin-1 antagonists, are used as novel therapeutic agents for the treatment of hearing loss, including presbycusis and other forms of sensorineural hearing loss. The present invention provides a method for inhibiting the action of TNF and/or IL-1 antagonists for treating hearing loss in a human by administering a TNF antagonist and/or an IL-1 antagonist for reducing the inflammation affecting the auditory apparatus of said human, or for modulating the immune response affecting the auditory apparatus of said human, by administering a therapeutically effective dosage level to said human of a TNF antagonist and/or an IL-1 antagonist. Administration may be systemic, through the subcutaneous, intramuscular, oral, or intravenous routes; or by delivering an anatomically localized application in the region of the head. The TNF antagonist is selected from the group consisting of etanercept, infliximab, D2E7, CDP 571, or thalidomide; and the IL-1 antagonist is either IL-1 RA or IL-1R type II receptor. Antiviral agents may be added for treating certain patients.

44 Claims, No Drawings

CYTOKINE ANTAGONISTS FOR THE TREATMENT OF SENSORINEURAL HEARING LOSS

RELATED APPLICATIONS

This is a continuation-in-part of application Ser. No. 09/654,996, filed on Sep. 5, 2000, which is a continuation-in-part of application Ser. No. 09/563,651, filed on May 2, 2000, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned.

FIELD OF THE INVENTION

The present invention is directed to specific cytokine antagonists, including TNF antagonists and IL-1 antagonists, for the treatment of hearing loss, including sensorineural hearing loss and presbycusis. The invention also includes methods of administration for these antagonists.

BACKGROUND OF THE INVENTION

Hearing loss occurs in humans in many forms. Hearing is essential to the normal conduct of one's daily activities and people with impaired hearing have many difficulties. Hearing loss can date from birth; it can be acquired later in life; or it can be the result of trauma, accident, disease, or a toxic effect of a medication. It can be genetic, either as a solitary disorder or as part of a complex syndrome. Hearing loss is one of the most common chronic neurological impairments, estimated to affect about 4 percent of those under 45 in the United States, and about 29 percent of those 65 years or older.

As defined herein, the auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids.

The pathogenetic mechanism of most forms of hearing loss has yet to be fully defined. Hearing loss can be due to conductive problems, which is not the subject of this patent; central hearing loss due to lesions of the central auditory pathway; or sensorineural hearing loss.

Humans react to sounds that are transduced into neurally conducted impulses through the action of neuroepithelial cells (hair cells) and spiral ganglion cells (neurons) in the inner ear. These impulses are transmitted along the cochlear division of the eighth cranial nerve into the brainstem and the central auditory pathways.

Presbycusis, or age-related hearing loss, is a type of sensorineural deafness which affects one-third of the population over the age of 75. The exact mechanism of presbycusis is unknown, and has long been thought to be multifactorial. Inflammation has not previously been thought to be a significant factor in the pathogenesis of presbycusis. Yet a previous study did suggest that genes encoded by the major histocompatibility complex (MHC) had a role in certain hearing disorders. (Bernstein, Acta Otolaryngol 1996 Sep; 116(5):666–71). The MHC is known to be central to the immune response and inflammation.

As will be discussed below there is now clinical evidence that inflammation has a role in the pathogenesis of various types of sensorineural hearing loss, including presbycusis. This opens up a new avenue of treatment of these disorders utilizing cytokine antagonists.

Monoclonal antibodies with a high affinity for a specific cytokine tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to interleukin-1 and tumor necrosis factor (TNF).

Cytokine antagonists can take several forms. They may be monoclonal antibodies (defined above); or in the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life.

Cytokine antagonists of the kind discussed in this patent play a central role in the inflammatory response and in immune injury. TNF is formed by the cleavage of a precursor transmembrane protein, forming soluble molecules, which aggregate to form trimolecular complexes. These complexes then bind to receptors found on a variety of cells. Binding produces an array of proinflammatory effects, including release of other pro-inflammatory cytokines, including interleukin (IL)-6, IL-8, and IL-1; release of matrix metalloproteinases; and up-regulation of the expression of endothelial adhesion molecules, further amplifying the inflammatory and immune cascade by attracting leukocytes into extravascular tissues. TNF is now well established as key in the pathogenesis of rheumatoid arthritis(RA) and Crohn's Disease, and new evidence of its involvement in other non-neurologic disorders and in other non-neurologic organ systems, such as the heart, is rapidly accumulating.

Tumor necrosis factor (TNF) is intimately involved in the nervous system. It is central to the response to injury, either virally induced, or occurring as a result of mechanical trauma. TNF is also central to neuronal apoptosis, a process important in many neurological disorders.

Specific inhibitors of TNF, only recently commercially available, now provide the possibility of therapeutic intervention in TNF mediated disorders. These antagonists, mainly developed to treat rheumatoid arthritis, include: 1) etanercept (Enbrel® sold by the Immunex Corporation), which is a recombinant fusion protein consisting of two soluble TNF receptors joined by the Fc fragment of a human IgGI molecule, for treating RA, Juvenile Rheumatoid Arthritis and Psoriatic Arthritis; 2) infliximab (Remicade® sold by Johnson and Johnson); and 3) D2E7, a human anti-TNF monoclonal antibody (sold by Knoll Pharmaceuticals). Other specific anti-TNF agents are under development, including CDP 571 (a chimeric, but 95% humanized, anti-TNF mAb), and a pegylated soluble TNF type 1 receptor.

Few effective therapeutic agents are available for the treatment of neurological disorders. The nervous system has only a limited capacity for repair. Neurological injury is therefore often permanent, irreversible, and clinically devastating. There is an urgent need for effective treatments of a wide variety of neurological conditions, many of which are chronic, progressive, and incurable. TNF modulation with these new agents offers a new modality of treatment for many of these disorders. Interleukin-1 (IL-1) is a proinflammatory cytokine which has been implicated in the inflammatory response occurring in the brain, spinal cord, retina, muscle, and elsewhere in the body. There are two naturally occurring inhibitors of IL-1 in the body: IL-1 receptor antagonist (IL-1 RA) and IL-1 receptor type II (IL-1 R type II). Interleukin-1 antagonists are in the process of being developed for clinical use in arthritis. The two specific agents which are of most relevance here are IL-1 RA (Anakinra, being developed by Amgen), and IL-1 R type II (Immunex).

The use of TNF antagonists and Interleukin antagonists for the treatment of neurological, retinal, optic nerve, and muscular disorders are the subject of pending patent applications by the author. The present invention covers using these agents to treat sensorineural hearing loss, and other forms of neurologically-mediated hearing loss.

There are various mechanisms whereby these cytokine antagonists may favorably influence the degree of hearing loss and the course and natural history of these disorders. The most direct mechanism is, of course, through their profound anti-inflammatory action. Inflammation can occur at any anatomic site in the auditory pathway, from the cochlea to the eighth cranial nerve to the brainstem or may even involve the higher auditory pathways of the brain. Additionally these agents may exert their beneficial effect through other mechanisms, such as through anti-apoptotic pathways. The exact locations at which these medications exert their beneficial effects for the treatment of hearing loss will undoutedly vary depending upon the specific hearing disorder being considered.

DESCRIPTION OF THE PRIOR ART

Pharmacologic chemical substances, compounds and agents having various organic structures and metabolic functions which are used for the treatment of sensorineural hearing loss, TNF related diseases, and IL-1 related diseases have been disclosed in the prior art. One example is U.S. Pat. No. 5,837,681, entitled "Method For Treating Sensorineural Hearing Loss Using Glial Cell Line-Derived Neurotrophic Factor (GDNF) Protein Product". However, this prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 6,043,221 entitled "Method For Preventing And Treating Hearing Loss Using A Neuturin Protein Product" discusses the use of a neurotrophic factor. This prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 5,385,901 entitled "Method Of Treating Abnormal Concentrations of TNF Alpha" discloses a method for the use of TNF antagonists. This prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 5,434,170 entitled "Method For Treating Neurocognitive Disorders" discloses the use of thalidomide to treat dementia. This prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 6,124,322 entitled "Intravenous Form Of Thalidomide For Treating Immunological Diseases" discloses a new aqueous form of thalidomide. This prior art patent does not teach the use of a TNF antagonist or interleukin-1 antagonist for the suppression and inhibition of the action of TNF and/or interleukin-1 in the human body to treat hearing loss as in the present invention.

U.S. Pat. No. 5,863,769 discloses the DNA sequence encoding IL-1 RA, and its use for treating various diseases. This prior art patent does not teach the use of an interleukin-1 antagonist for the suppression and inhibition of the action of interleukin-1 in the human body to treat hearing loss as in the present invention.

U.S. Pat. No. 5,075,222 discloses the DNA sequences encoding IL-1 inhibitors. This prior art patent does not teach the use of an interleukin-1 antagonist for the suppression and inhibition of the action of interleukin-1 in the human body to treat hearing loss, as in the present invention.

U.S. Pat. No. 5,605,690 discloses a method for treating TNF-dependent inflammatory diseases, such as arthritis, by administering a TNF antagonist, such as soluble human TNFR (a sequence of amino acids), to a human. This prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 5,656,272 discloses methods of treating TNF-alpha-mediated Crohn's disease using chimeric anti-TNF antibodies. This prior art patent does not teach the use of a TNF antagonist or interleukin-1 antagonist for the suppression and inhibition of the action of TNF and/or interleukin-1 in the human body to treat hearing loss, as in the present invention.

U.S. Pat. No. 5,559,114 discloses the use of acyclovir and famciclovir at higher than normal doses to treat autoimmune disease. This prior art patent does not teach the use of antiviral drugs combined with a cytokine antagonist in the human body to treat hearing loss, as in the present invention.

None of these prior art patents teach the use of a TNF antagonist or an interleukin-1 antagonist for the suppression or inhibition of the action of TNF and/or interleukin-1 in the human body to treat hearing loss, as in the present invention.

Accordingly, it is an object of the present invention to provide a TNF antagonist, and/or an interleukin-1 antagonist, for treating hearing loss in a human, wherein the use of these antagonists results in the amelioration of hearing loss in a human.

Another object of the present invention to provide a TNF antagonist for the treatment of presbycusis in a human such that the use of this antagonist results in improved hearing.

Another object of the present invention to provide a TNF antagonist for the treatment of sensorineural hearing loss in a human such that the use of this antagonist results in improved hearing.

Another object of the present invention to provide a TNF antagonist for the treatment of sensorineural hearing loss in a human such that the use of this antagonist results in improved hearing without the use of a hearing aid, in a manner that is both safe and effective.

Another object of the present invention to provide a TNF antagonist and/or interleukin-1 antagonist for the treatment of hearing loss in a human such that the use of this antagonist results in improved hearing without the need for surgery.

Another object of the present invention is to provide novel and improved routes of administration for the selected TNF antagonist and/or interleukin-1 antagonist for the treatment of sensorineural hearing loss in a human such that the use of this antagonist with this method results in improved hearing in a manner that is both safe, effective, and economical.

Another object of the present invention to provide a TNF antagonist in combination with an interleukin-1 antagonist for the treatment of sensorineural hearing loss in a human such that the use of these antagonists together results in improved hearing, to an extent greater than the use of either one of these agents alone.

SUMMARY OF THE INVENTION

The present invention provides methods for treating hearing loss in a human comprising administering to a subject experiencing hearing loss a therapeutically effective amount of a specific cytokine antagonist, chosen from a selected group of TNF antagonists and interleukin-1 antagonists. These agents may be used alone or in combination to improve hearing in humans with hearing loss due to a variety of causes, including presbycusis, other forms of sensorineural hearing loss, and central hearing loss. These specific cytokine antagonists are biologic agents and are administered through a variety of routes, including subcutaneous, intravenous, and several novel routes of administration.

It is contemplated that these specific cytokine antagonists can be administered alone or in combination. Furthermore, it is contemplated that some patients may require chronic treatment, whereas others may respond to a short course of treatment that results in sustained improvement even after the medication is withdrawn. Additionally, it is contemplated that some patients may benefit from the addition of an antiviral agent to the treatment regimen.

The demonstrated usefullness of this class of biologic medications for the treatment of hearing loss suggests a significant role of inflammation in the pathogenesis of these disorders.

DETAILED DESCRIPTION OF THE PREFERRED EMBODIMENTS

Presbycusis, or age-related hearing loss, affects one-third of the U.S. population over age 75, and presents a significant hardship to these people, many of whom are faced with the burden of other age-related illnesses. At this time, it is difficult to determine the degree to which any individual patient will respond to treatment with the cytokine antagonists discussed herein. The advantages of using etanercept are its rapid onset of action, general lack of side effects, ease of administration, and relatively low cost per dose. For adult patients the dose will uniformly be 25 mg, administered subcutaneously in the same manner as with Rheumatoid Arthritis patients, i.e. into the abdominal area or the thigh. Some patients may have a better response from subcutaneous injection directly overlying the mastoid process. For these patients it is recommended that the side of the head be rotated with each dose, i.e. one dose on the right side of the head, and the next dose on the left side, etc. Some patients will respond to a lower dose, in the range of 5 mg to 15 mg, when etanercept is administered directly to the mastoid area. For all patients dosing is continued twice per week with the same dose. Etanercept administration is discontinued if the patient develops an infection at any site, and is not started in any patient that has an infection.

D2E7 is a fully human anti-TNF antibody. D2E7 is administered in exactly the same way as etanercept, with the same precautions. The only difference is the dose interval and the dosage. D2E7 for presbycusis will usually be administered at a starting dose of 20 mg subcutaneously given once every two weeks. The effective dose and interval may vary, according to individual response, from as little as 10 mg administered once per month to as much as 20 mg given weekly. As with etanercept, some patients may have a better response from subcutaneous injection directly overlying the mastoid process.

CDP-571 is a TNF antagonist in clinical development. It is a monoclonal antibody, and for purposes of this patent, it functions in a manner similar to infliximab. The intravenous route of administration is currently the preferred method for infliximab. Infliximab carries with it the advantage of reimbursement by additional third parties, and the advantage of a longer interval between doses than either etanercept or D2E7. The dosage regimen for infliximab recommended for initial use is the same as that recommended by the manufacturer for the treatment of arthritis, i.e. 3 mg/kg given as an intravenous infusion followed with additional 3 mg/kg doses at 2 and 6 weeks after the first infusion, then every 8 weeks thereafter. Because infliximab is a chimeric monoclonal antibody, with a mouse component, human anti-chimeric antibodies (HACA) may develop. Methotrexate has been shown to reduce the development of HACA. For this reason, methotrexate may need to be administered with infliximab.

Thalidomide is also beneficial for certain patients. The recommended starting dose is 50 mg orally taken once per day. Patients not responding can have their dose escalated monthly by a 50 mg increment, up to a maximum of 200 mg per day. A new aqueous formulation of thalidomide may allow the use of subcutaneous dosing. In this case, patients could be given a lower dosage, especially if injected subcutaneously in the area overlying the mastoid.

Certain patients may respond to the use of interleukin-1 antagonists, used instead of a TNF antagonist. The two medications in this class to be used here are IL-1 RA (anakira, A mgen) and IL-1 R type II (Immunex). The recommended dosage and dose interval are similar to the parameters recommended for their use for Rheumatoid Arthritis.

Some patients will receive additional therapeutic benefit from the use of a TNF antagonist administered with an interleukin-1 antagonist. The use of these medications in this manner has been demonstrated to be synergistic when used to treat an arthritis model in animals. The combination produces a more potent anti-inflammatory effect than when either agent is administered alone.

Patients with other forms of sensorineural hearing loss, and patients with central hearing loss are treated in the same manner as those with Presbycusis discussed above. The only difference will be the dosages, which in children will need to be adjusted appropriately for the patient's lean body mass.

Certain patients with selected forms of sensorineural and/or central hearing loss, including certain patients with presbycusis, will benefit from the addition of an antiviral agent in addition to a cytokine antagonist. This is because certain forms of hearing loss are due to focal infection of a locus of the auditory pathway by a neurotropic virus. Known neurotropic viruses include those in the herpes family, especially herpes simplex 1 and 2, human herpes virus 6, and varicella-zoster. These viruses can involve the neural components of the auditory pathway, such as the eighth cranial nerve, and thereby produce either sudden sensorineural hearing loss (in the case of acute infection) or chronic, progressive hearing loss (in the case of low-grade, chronic viral involvement). Certain patients will therefore require acute therapy, and others will require chronic therapy with antiviral agents, such as famciclovir, acyclovir, or valacyclovir. Antiviral therapy in combination with cytokine antagonists is the subject of a previous patent application by the inventor.

Idiopathic sudden sensorineural hearing loss is a known clinical entity. The only treatment with reported success is the use of corticosteroids. Some of these cases are thought to have viral causation. The use of a cytokine antagonist in combination with an antiviral medication may prove beneficial for these patients. No studies of this combination for this clinical condition have been published. The recommended regimen would be etanercept 25 mg subcutaneously twice a week in combination with valacyclovir 1 gram po BID for one month, with tapering as needed.

For children, there are additional considerations. Sensorineural hearing loss is an important cause of disability in children. Many of the causes are genetic, and these can lead to profound deafness. Those disorders with a known component of inflammation should give the best response to the antagonists disclosed herein. Etanercept has proven to be both safe and effective for chronic use for arthritis in children. The aforementioned caveats with regard to infection apply to children as well as to adults. D2E7 is also a therapy for use in children. For certain neurotropic viral infections of children, the combination of cytokine antagonists with antiviral medications will reduce or, even in some cases, prevent the development of hearing loss.

EXAMPLE 1

Etanercept for the Treatment of Sensorineural Hearing Loss

A 73 year old Caucasian woman patient presented with a history of slowly increasing hearing loss in both ears. The patient had noticed decreasing hearing beginning approximately 20 years earlier, in her 50's. Her father had experienced hearing loss beginning about the same age. One year prior the patient had noticed that she was having great difficulty hearing conversation when at family meetings. Her grandchildren were urging her to get hearing aids about that time. Six months prior to her visit she obtained digital hearing aids, and used them daily. The patient had a recent history of sciatica; a history of spinal stenosis; and a previous diagnosis of sensorineural hearing loss. A subcutaneous injection of etanercept was administered at a dose of 25 mg. One hour later the patient noticed that sounds were significantly louder. Improved hearing continued for the duration of treatment with etanercept. One day after receiving the second dose of etanercept 25 mg, which was administered four days after the first dose, the patient needed to remove her digital hearing aids because her hearing was so improved that sounds were too loud while the hearing aids were in place. This had not been necessary during the entire time of use of these hearing aids, prior to her treatment with etanercept.

METHODS OF ADMINISTRATION AND DOSAGE LEVELS

For treating the above diseases with the above-mentioned TNF antagonists, these TNF antagonists may be administered by the following routes:

The above TNF antagonists may be administered subcutaneously in the human and the dosage level is in the range of 5 mg to 50 mg for acute or chronic regimens.

The above TNF antagonists may be administered intranasally in the human and the dosage level is in the range of 0.1 mg to 10 mg for acute or chronic regimens.

The above TNF antagonists may be administered intramuscularly in the human and the dosage level is in the range of 25 mg to 100 mg.

The above TNF antagonists may be administered intravenously in the human and the dosage level is in the range of 2.5 mg/kg to 20 mg/kg.

The above TNF antagonists may be administered transepidermally in the human and the dosage level is in the range of 10 mg to 100 mg.

The above TNF antagonists may be administered by inhaling by the human and the dosage level is in the range of 0.2 mg to 40 mg.

The above TNF antagonists may be administered orally by the human and the dosage level is in the range of 10 mg to 300 mg.

Etanercept is administered intramuscularly in a human wherein the dosage level is in the range of 25 mg to 100 mg.

Infliximab is administered intravenously in a human wherein the dosage level is in the range of 2.5 mg/kg to 20 mg/kg.

Etanercept is administered subcutaneously in a human wherein the dosage level is in the range of 5 mg to 50 mg.

The thalidomide group is administered orally to a human wherein the dosage level is in the range of 10 mg to 300 mg.

The above TNF antagonists may be administered at a dosage interval of from once a day to once every six months.

Etanercept is usually administered twice a week; with a range from twice a week to once per week.

D2E7 is usually administered twice a month, with a range from once a week to once per month.

IL-1 RA is usually administered three times a week, with a range from once per day to once per week.

The usual subcutaneous dose of etanercept is 25 mg twice per week.

The usual subcutaneous dose of D2E7 is 20 mg, with a range from 5 mg to 40 mg.

IL-1 RA and IL-1 R type II dosages are similar and are approximately 0.02 to 3.0 mg/kg when given daily by subcutaneous bolus injection.

The usual dosage and route of administration for famciclovir is 500 mg given orally either BID or TID.

The usual dosage and route of administration for valaciclovir is 500 mg to 1 gram given orally BID.

The usual dosage and route of administration for acyclovir is 400 mg to 800 mg given orally every 5 hours. For idiopathic sudden sensorineural hearing loss it may also be administered intravenously.

ADVANTAGES OF THE PRESENT INVENTION

Accordingly, an advantage of the present invention is to provide a TNF antagonist, and/or an interleukin-1 antagonist, for treating hearing loss in a human, wherein the use of these antagonists results in the amelioration of hearing loss in a human.

Another advantage of the present invention is that it provides a TNF antagonist for the treatment of presbycusis in a human such that the use of this antagonist results in improved hearing.

Another advantage of the present invention is that it provides a TNF antagonist for the treatment of sensorineural hearing loss in a human such that the use of this antagonist results in improved hearing.

Another advantage of the present invention is that it provides a TNF antagonist for the treatment of sensorineural hearing loss in a human such that the use of this antagonist results in improved hearing without the use of a hearing aid, in a manner that is both safe and effective.

Another advantage of the present invention is that it provides a TNF antagonist and/or interleukin-1 antagonist for the treatment of hearing loss in a human such that the use of this antagonist results in improved hearing without the need for surgery.

Another advantage of the present invention is that it provides a TNF antagonist and an interleukin-1 antagonist for the treatment of sensorineural hearing loss in a human such that the use of these antagonists together results in improved hearing, to an extent greater than the use of either one of these agents alone.

Another advantage of the present invention is that it provides a TNF antagonist and an anti-viral medication for the treatment of sensorineural hearing loss in a human such that the use of these medications together results in improved hearing, to an extent greater than the use of either one of these agents alone.

Another advantage of the present invention is that it provides novel and improved routes of administration for the selected TNF antagonist and/or interleukin-1 antagonist for the treatment of sensorineural hearing loss in a human such that the use of this antagonist in this manner results in improved hearing with a method that is both safe, effective, and economical.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

REFERENCES

Adams et al. (1989), "Deafness, Dizziness, and Disorders of Equilibrium," Principles of Neurology Ch.14:226–246.

Arck, P. C., Troutt, A. B., Clark, D. A. (1997). Soluble receptors neutralizing TNF-a and IL-1 block stress-triggered murine abortion. Am J Reprod Immunol 37, 262–266.

Colotta F, Re F, Muzio M, Bertini R, Polentarutti N, Sironi M, Giri J G,Dower S K, Sims J E, Mantovani A. Interleukin-1 type II receptor: a decoy target for IL-1 that is regulated by IL-4. Science 1993;261:472–5.

Dinarello C A. Interleukin-1, interleukin-1 receptors and interleukin-1 receptor antagonist. International Reviews of Immunology 1998;16:457–99.

Eldman N, Brennan F M, Maini R N. The role of cytokines in rheumatoid arthritis. Ann Rev Immunol 1996;14:397.

Hefti (1994), "Neurotrophic Factor Therapy for Nervous System Degenerative Diseases," J. Neurobiol. 25:1418–1435.

Lovell D J, Giannini E H, Reiff, A, et al. Etanercept in children with polyarticular juvenile rheumatoid arthritis. N Engl J Med 2000;342(11):763–9.

Murray, K. M., Dahl, S. L. (1997). Recombinant human tumor necrosis factor receptor (p75) fusion protein (TNFR:Fc) in rheumatoid arthritis. Ann Pharmacother 31, 1335–1338.

Mohler, K. M., Torrance, D. S., Smith, C. A., Goodwin, R. G., Stremler, K. E., Fung, V. P., Madani, H., Widmer, M. B. (1993). Soluble tumor necrosis factor (TNF) receptors are effective therapeutic agents in lethal endotoxemia and function simultaneously as both TNF carriers and TNF antagonists. J Immunol 151, 1548–1561.

Nadol (1981) "The Aging Peripheral Hearing Mechanism," Aging: Communication Processes and Disorders Ch. 4:63–85.

Nadol (1993), "Hearing Loss," New England J. of Medicine 329:1092–1102.

Schuknecht (1974) Pathology of the Ear pp. 388–403.

Sims J E, Gayle M A, Slack J L, Alderson M R, Bird T A, Giri J G, Colotta F, Re F, Mantovani A, Shanebeck K, Grabstein K H, Dower S K. Interleukin 1 signaling occurs exclusively via the type I receptor. Proc Natl Acad Sci U S A 1993;90:6155–9.

Spoendlin (1984), "Primary Neurons and Synapses," Ultrastructural Atlas of the Inner Ear Ch. 6:133–164.

Wiley, S. R., Schooley, K., Smolak, P. J., Din, W. S., Huang, C.-P., Nicholl, J. K., Sutherland, G. R., Davis Smith, T., Rauch, C., Smith, C. A., Goodwin, R. G. (1995). Identification and characterization of a new member of the TNF family that induces apoptosis. Immunity 3, 673–682.

Wilson et al. (1980), "The Efficacy of Steroids in the Treatment of Idopathic Sudden Hearing Loss," Arch Otolaryngol 106:772–776.

Wooley P H, Dutcher J, Widmer M B, et al. Influence of a recombinant human soluble tumor necrosis factor receptor FC fusion protein on type II collagen-induced arthritis in mice. J Immunol 1993;151:6602.

What is claimed is:

1. A method for inhibiting the action of TNF for treating sensorineural hearing loss in a human by administering etanercept for reducing the inflammation affecting the auditory apparatus of said human, or for modulating the immune response affecting the auditory apparatus of said human, comprising the step of:

a) administering a therapeutically effective dosage level to said human of said etanercept for reducing the inflammation affecting the auditory apparatus of said human, or for modulating the immune response affecting the auditory apparatus of said human.

2. A method for inhibiting the action of TNF in accordance with claim 1, wherein the step of administering said etanercept is performed by delivering said therapeutically effective dosage level through the subcutaneous route.

3. A method for inhibiting the action of TNF in accordance with claim 1, wherein the step of administering said etanercept is performed subcutaneously in said human wherein said dosage level is in the range of 5 mg to 50 mg.

4. A method for inhibiting the action of TNF in accordance with claim 1, wherein the step of administering said etanercept is performed subcutaneously by delivering said etanercept dose to the subcutaneous tissue overlying one of the mastoid processes of said human.

5. A method for inhibiting the action of TNF for treating sensorineural hearing loss in a human by administering D2E7 for reducing the inflammation affecting the auditory apparatus of said human, or for modulating the immune response affecting the auditory apparatus of said human, comprising the step of:

a) administering a therapeutically effective dosage level to said human of said D2E7 for reducing the inflammation affecting the auditory apparatus of said human, or for modulating the immune response affecting the auditory apparatus of said human.

6. A method for inhibiting the action of TNF in accordance with claim 5, wherein the step of administering said D2E7 is performed by delivering said therapeutically effective dosage level through the subcutaneous route.

7. A method for inhibiting the action of TNF in accordance with claim 5, wherein the step of administering said D2E7 is performed subcutaneously in said human wherein said dosage level is in the range of 5 mg to 50 mg.

8. A method for inhibiting the action of TNF in accordance with claim 5, wherein the step of administering said D2E7 is performed subcutaneously by delivering said D2E7 dose to the subcutaneous tissue overlying one of the mastoid processes of said human.

9. A method for inhibiting the action of TNF in accordance with claim 5, wherein the step of administering said DE27 is performed by delivering a therapeutically effective dosage level through the intravenous route.

10. A method for inhibiting the action of TNF for treating sensorineural hearing loss in a human by administering infliximab for reducing the inflammation affecting the auditory apparatus of said human, or for modulating the immune response affecting the auditory apparatus of said human, comprising the step of:
   a) administering a therapeutically effective dosage level to said human of said infliximab for reducing the inflammation affecting the auditory apparatus of said human, or for modulating the immune response affecting the auditory apparatus of said human.

11. A method for inhibition the action of TNF in accordance with claim 10, wherein the step of administering said infliximab is performed by delivering a therapeutically effective dosage level through the subcutaneous route.

12. A method for inhibiting the action of TNF in accordance with claim 10, wherein the step of administering said infliximab is performed subcutaneously in said human wherein said dosage level is in the range of 5 mg to 50 mg.

13. A method for inhibiting the action of TNF in accordance with claim 10, wherein the step of administering said infliximab is performed subcutaneously by delivering said infliximab dose to the subcutaneous tissue overlying one of the mastoid processes of said human.

14. A method for inhibiting the action of TNF in accordance with claim 10, wherein the step of administering said infliximab is performed by delivering a therapeutically effective dosage level through the intravenous route.

15. A method for inhibiting the action of TNF in accordance with claim 10, wherein the step of administering said infliximab is performed intravenously in said human wherein said dosage level is in the range of 1.0 mg/kg to 20 mg/kg.

16. A method for inhibiting the action of TNF for treating presbycusis in a human by administering etanercept for reducing the inflammation affecting the auditory apparatus of said human, or for modulating the immune response affecting the auditory apparatus of said human, comprising the step of:
   a) administering a therapeutically effective dosage level to said human of said etanercept for reducing the inflammation affecting the auditory apparatus of said human, or for modulating the immune response affecting the auditory apparatus of said human.

17. A method for inhibiting the action of TNF for treating presbycusis in a human by administering D2E7 for reducing the inflammation affecting the auditory apparatus of said human, or for modulating the immune response affecting the auditory apparatus of said human, comprising the step of:
   a) administering a therapeutically effective dosage level to said human of said D2E7 for reducing the inflammation affecting the auditory apparatus of said human, or for modulating the immune response affecting the auditory apparatus of said human.

18. A method for inhibiting the action of TNF for treating presbycusis in a human by administering infliximab for reducing the inflammation affecting the auditory apparatus of said human, or for modulating the immune response affecting the auditory apparatus of said human, comprising the step of:
   a) administering a therapeutically effective dosage level to said human of said infliximab for reducing the inflammation affecting the auditory apparatus of said human, or for modulating the immune response affecting the auditory apparatus of said human.

19. A method for inhibiting the action of TNF in accordance with claim 16, wherein the step of administering said etanercept is performed by delivering said therapeutically effective dosage level through the subcutaneous route.

20. A method for inhibiting the action of TNF in accordance with claim 16, wherein the step of administering said etanercept is performed subcutaneously in said human wherein said dosage level is in the range of 5 mg to 50 mg.

21. A method for inhibiting the action of TNF in accordance with claim 16, wherein the step of administering said etanercept is performed subcutaneously by delivering said etanercept dose to the subcutaneous tissue overlying one of the mastoid processes of said human.

22. A method for inhibiting the action of TNF for treating hearing loss in a human by administering etanercept for reducing the inflammation affecting the auditory apparatus of said human, or for modulating the immune response affecting the auditory apparatus of said human, comprising the step of:
   a) administering a therapeutically effective dosage level to said human of said etanercept for reducing the inflammation affecting the auditory apparatus of said human, or for modulating the immune response affecting the auditory apparatus of said human.

23. A method for inhibiting the action of TNF for treating hearing loss in a human by administering D2E7 for reducing the inflammation affecting the auditory apparatus of said human, or for modulating the immune response affecting the auditory apparatus of said human, comprising the step of:
   a) administering a therapeutically effective dosage level to said human of said D2E7 for reducing the inflammation affecting the auditory apparatus of said human, or for modulating the immune response affecting the auditory apparatus of said human.

24. A method for inhibiting the action of interleukin-1 for treating hearing loss in a human by administering IL-1 RA for reducing the inflammation affecting the auditory apparatus of said human, or for modulating the immune response affecting the auditory apparatus of said human, comprising the step of:
   a) administering a therapeutically effective dosage level to said human of said IL-1 RA for reducing the inflammation affecting the auditory apparatus of said human, or for modulating the immune response affecting the auditory apparatus of said human.

25. A method for inhibiting the action of interleukin-1 for treating hearing loss in a human by administering IL-1 R type II for reducing the inflammation affecting the auditory apparatus of said human, or for modulating the immune response affecting the auditory apparatus of said human, comprising the step of:

a) administering a therapeutically effective dosage level to said human of said IL-1 R type II for reducing the inflammation affecting the auditory apparatus of said human, or for modulating the immune response affecting the auditory apparatus of said human.

26. A method for inhibiting the action of TNF for treating hearing loss in a human by administering thalidomide for reducing the inflammation affecting the auditory apparatus of said human, or for modulating the immune response affecting the auditory apparatus of said human, comprising the step of:
   a) administering a therapeutically effective dosage level to said human of said thalidomide for reducing the inflammation affecting the auditory apparatus of said human, or for modulating the immune response affecting the auditory apparatus of said human.

27. A method for inhibiting the action of TNF for treating hearing loss in a human by administering infliximab for reducing the inflammation affecting the auditory apparatus of said human, or for modulating the immune response affecting the auditory apparatus of said human, comprising the step of:
   a) administering a therapeutically effective dosage level to said human of said infliximab for reducing the inflammation affecting the auditory apparatus of said human, or for modulating the immune response affecting the auditory apparatus of said human.

28. A method for inhibiting the action of TNF and interleukin-1 for treating hearing loss in a human by administering a TNF antagonist and an interleukin-1 antagonist for reducing the inflammation affecting the auditory apparatus of said human, or for modulating the immune response affecting the auditory apparatus of said human, comprising the steps of:
   a) administering a therapeutically effective dosage level to said human of said TNF antagonist for reducing the inflammation affecting the auditory apparatus of said human, or for modulating the immune response affecting the auditory apparatus of said human; and
   b) administering a therapeutically effective dosage level to said human of said interleukin-1 antagonist for reducing the inflammation affecting the auditory apparatus of said human, or for modulating the immune response affecting the auditory apparatus of said human.

29. A method for inhibiting the action of TNF and interleukin-1 in accordance with claim 28, wherein the step of administering said TNF antagonist is performed by delivering a therapeutically effective dose of etanercept.

30. A method for inhibiting the action of TNF and interleukin-1 in accordance with claim 28, wherein the step of administering said TNF antagonist is performed by delivering a therapeutically effective dose of D2E7.

31. A method for inhibiting the action of TNF and interleukin-1 in accordance with claim 28, wherein the step of administering said interleukin-1 antagonist is performed by delivering a therapeutically effective dose of IL-1 RA.

32. A method for inhibiting the action of TNF and interleukin-1 in accordance with claim 28, wherein the step of administering said interleukin-1 antagonist is performed by delivering a therapeutically effective dose of IL-1 R type II.

33. A method for inhibiting the action of TNF and interleukin-1 in accordance with claim 28, wherein the step of administering said interleukin-1 antagonist is performed by delivering a therapeutically effective dose of IL-1 RA, and the step of administering said TNF antagonist is performed by administering a therapeutically effective dose of etanercept.

34. A method for inhibiting the action of TNF for treating hearing loss in a human by administering a TNF antagonist selected from the group consisting of etanercept, infliximab, D2E7, or CDP 571 for reducing the inflammation affecting the auditory apparatus of said human, or for modulating the immune response affecting the auditory apparatus of said human, comprising the step of:
   a) administering a therapeutically effective dosage level to said human of said TNF antagonist by delivering an anatomically localized application in the region of the head for reducing the inflammation affecting the auditory apparatus of said human, or for modulating the immune response affecting the auditory apparatus of said human, wherein the TNF antagonist is selected from the group consisting of etanercept, infliximab, D2E7, or CDP 571.

35. A method for inhibiting the action of TNF in accordance with claim 34, wherein said TNF antagonist is administered by delivering a local ear instillation via ear drops in a therapeutically effective dose.

36. A method for inhibiting the action of TNF in accordance with claim 34, wherein said TNF antagonist is administered by delivering through the transepidermal route in a therapeutically effective dose.

37. A method for inhibiting the action of TNF in accordance with claim 34, wherein the step of administering said TNF antagonist is performed transepidermally in said human wherein said dosage level is in the range of 10 mg to 100 mg.

38. A method for inhibiting the action of TNF in accordance with claim 34, wherein said TNF antagonist is delivered by transmucosal administration.

39. A method for inhibiting the action of TNF for treating hearing loss in a human by administering a TNF antagonist for reducing the inflammation affecting the auditory apparatus of said human, or for modulating the immune response affecting the auditory apparatus of said human, comprising the step of:
   a) administering a therapeutically effective dosage level to said human of said TNF antagonist for reducing the inflammation affecting the auditory apparatus of said human, or for modulating the immune response affecting the auditory apparatus of said human.

40. A method for inhibiting the action of interleukin-1 for treating hearing loss in a human by administering an interleukin-1 antagonist for reducing the inflammation affecting the auditory apparatus of said human, or for modulating the immune response affecting the auditory apparatus of said human, comprising the step of:
   a) administering a therapeutically effective dosage level to said human of said interleukin-1 antagonist for reducing the inflammation affecting the auditory apparatus of said human, or for modulating the immune response affecting the auditory apparatus of said human.

41. A method for inhibiting the action of TNF for treating hearing loss in a human by administering a TNF antagonist and an antiviral medication for reducing the inflammation affecting the auditory apparatus of said human, or for modulating the immune response affecting the auditory apparatus of said human, comprising the steps of:
   a) administering a therapeutically effective dosage level to said human of said TNF antagonist for reducing the inflammation affecting the auditory apparatus of said human, or for modulating the immune response affecting the auditory apparatus of said human, and;
   b) administering a therapeutically effective dosage level to said human of said antiviral medication for reducing the inflammation affecting the auditory apparatus of said human, or for modulating the immune response affecting the auditory apparatus of said human.

42. A method for treating hearing loss in a human in accordance with claim 41, wherein said TNF antagonist is etanercept.

43. A method for treating hearing loss in a human in accordance with claim 41, wherein said antiviral medication is selected from the group consisting of famciclovir, acyclovir, and valaciclovir.

44. A method for treating hearing loss in a human, comprising the steps of:
   a) administering a therapeutically effective dose to said human of etanercept; and
   b) administering a therapeutically effective dose to said human of an antiviral agent selected from the group consisting of famciclovir, acyclovir, and valaciclovir.

* * * * *